United States Patent
Francis et al.

(10) Patent No.: US 7,211,054 B1
(45) Date of Patent: May 1, 2007

(54) METHOD OF TREATING A PATIENT WITH A NEURODEGENERATIVE DISEASE USING ULTRASOUND

(75) Inventors: Charles W. Francis, Rochester, NY (US); Valentina Suchkova, Macedon, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 09/435,286

(22) Filed: Nov. 5, 1999

Related U.S. Application Data

(60) Provisional application No. 60/107,383, filed on Nov. 6, 1998.

(51) Int. Cl.
*A61N 7/00* (2006.01)

(52) U.S. Cl. .......................................... 601/2

(58) Field of Classification Search ............... 601/2–4; 600/439, 466, 467; 607/50, 51, 99; 604/22, 604/280
See application file for complete search history.

(56) References Cited

U.S. PATENT DOCUMENTS

| | | | |
|---|---|---|---|
| 3,828,769 A * | 8/1974 | Mettler ........................... | 601/2 |
| 3,951,136 A * | 4/1976 | Wall ............................... | 600/380 |
| 4,354,502 A * | 10/1982 | Colley et al. ................ | 600/469 |
| 4,646,725 A * | 3/1987 | Moasser ....................... | 601/2 |
| 4,651,716 A * | 3/1987 | Forester et al. ............... | 601/2 |
| 4,889,122 A | 12/1989 | Watmough et al. | |
| 4,890,619 A | 1/1990 | Hatschek | |
| 5,249,580 A | 10/1993 | Griffith | |
| 5,291,894 A | 3/1994 | Nagy | |
| 5,324,255 A | 6/1994 | Passafaro et al. | |
| 5,413,550 A | 5/1995 | Castel | |
| 5,427,118 A | 6/1995 | Nita et al. | |
| 5,472,406 A | 12/1995 | de la Torre et al. | |
| 5,520,612 A * | 5/1996 | Winder et al. ................. | 601/2 |
| 5,620,409 A | 4/1997 | Venuto et al. | |
| 5,690,608 A | 11/1997 | Watanabe et al. | |
| 5,692,509 A | 12/1997 | Voss et al. | |
| 5,713,831 A * | 2/1998 | Olsson ........................... | 601/2 |
| 5,755,764 A * | 5/1998 | Schroeppel ................. | 607/122 |
| 5,827,203 A | 10/1998 | Nita | |
| 5,846,517 A * | 12/1998 | Unger ........................ | 424/9.52 |
| 5,904,938 A * | 5/1999 | Zapol et al. ................. | 424/718 |
| 6,071,303 A * | 6/2000 | Laufer ......................... | 607/96 |
| 6,110,098 A * | 8/2000 | Renirie et al. ............... | 600/16 |

(Continued)

FOREIGN PATENT DOCUMENTS

WO    WO 93/15670    * 8/1993

OTHER PUBLICATIONS

Olsson et al. "Enhancement of Thrombolysis by Ultrasound" (1994) Ultrasound in Med. & Biol. vol. 20, No. 4, pp. 375-382.*

(Continued)

*Primary Examiner*—Ruth S. Smith
(74) *Attorney, Agent, or Firm*—Nixon Peabody LLP

(57) ABSTRACT

The present invention provides methods for treating patients with ultrasound to promote healing. In particular, the present invention provides a method for improving blood flow to ischemic tissue by applying ultrasound to ischemic tissue. The invention also provides a method for increasing nitric oxide production in tissue by applying ultrasound to tissue.

7 Claims, 13 Drawing Sheets

U.S. PATENT DOCUMENTS

| | | | | |
|---|---|---|---|---|
| 6,166,092 | A * | 12/2000 | Sekins et al. | 514/772 |
| 6,218,366 | B1 * | 4/2001 | St. Cyr et al. | 514/23 |
| 6,224,584 | B1 * | 5/2001 | March et al. | 604/508 |
| 6,273,864 | B1 * | 8/2001 | Duarte et al. | 601/2 |
| 6,398,772 | B1 * | 6/2002 | Bond et al. | 604/507 |
| 6,575,922 | B1 * | 6/2003 | Fearnside et al. | 601/2 |

OTHER PUBLICATIONS

Vashkevich, "The Ultrasonic Therapy of Patients with Arteriosclerosis Obliterans of the Vessels of the Lower Extremities," *Vopr Kurotol Fizioter Lech Fiz Kult*, 1:32-36 (1991).

Siegel et al., "Use of Therapeutic Ultrasound in Percutaneous Coronary Angioplasty. Experimental In vitro Studies and Initial Clinical Experience," *Circulation*, 89(4):1587-1592 (1994).

Suchkova et al., "Enhancement of Fibrinolysis with 40-kHz Ultrasound," *Circulation*, 98(10):1030-1035 (1998).

Siegel et al., "Clinical Demonstration That Catheter-Delivered Ultrasound Energy Reverses Arterial Vasoconstriction," *JACC*, 20(3):732-735 (1992).

Suchkova et al., "Effect of 40-kHz Ultrasound on Acute Thrombotic Ischemia in a Rabbit Femoral Artery Thrombosis Model," *Circulation* pp. 2296-2301 (2000).

Siddiqi et al., "Binding of Tissue-Plasminogen Activator to Fibrin: Effect of Ultrasound," *Blood* 91(6):2019-2025 (1998).

Braaten et al., "Ultrasound Reversibly Disaggregates Fibrin Fibers," *Thromb Haemost* 78:1063-8 (1997).

Riggs et al., "Ultrasound Enhancement of Rabbit Femoral Artery Thrombolysis," *Cardiovascular Surgery* 5(2):201-207 (1997).

Harpaz et al., "Ultrasound Enhancement of Thrombolysis and Reperfusion In Vitro," *JACC* 21(6):1507-11 (1993).

Harpaz et al., "Ultrasound Accelerates Urokinase-Induced Thrombolysis and Reperfusion," *American Heart Journal* 127(5):1211-1219 (1994).

Kashyap et al., "Acceleration of Fibrinolysis by Ultrasound in a Rabbit Ear Model of Small Vessel Injury," *Thrombosis Research* 76(5):475-485 (1994).

Siddiqi et al., "Ultrasound Increases Flow Through Fibrin Gels," *Thrombosis and Haemostasis* 73(3):495-8 (1995).

Francis et al., "Ultrasound Accelerates Transport of Recombinant Tissue Plasminogen Activator into Clots," *Ultrasound in Med. & Biol.* 21(3):419-424 (1995).

Blinc et al., "Characterization of Ultrasound-Potentiated Fibrinolysis In Vitro," *Blood* 81(10):2636-2643 (1993).

Steffen et al., "Catheter-delivered High Intensity, Low Frequency Ultrasound Induces Vasodilation In Vivo," *European Heart Journal* 15:369-376 (1994).

Francis et al., "Enhancement of Fibrinolysis In Vitro by Ultrasoundm" *J. Clin. Invest.* 90:2063-2068 (1992).

Bredt et al., "Nitric Oxide: A Physiologic Messenger Molecule," *Annu. Rev. Biochem.* 63:175-195 (1994).

Cooke et al., "Derangements of the Nitric Oxide Synthase Pathway, L-Arginine, and Cardiovascular Diseases," *Circulation* 96(2):379-382 (1997).

Christopherson et al., "Nitric Oxide in Excitable Tissues: Physiological Roles and Disease," *J. Clin Invest.* 100(10):2424-2429 (1997).

* cited by examiner

METHOD OF TREATING A PATIENT WITH A NEURODEGENERATIVE DISEASE USING ULTRASOUND

The present application claims the benefit of U.S. Provisional Patent Application Ser. No. 60/107,383, filed Nov. 6, 1998.

The subject matter of this application was made with support from the United States Government under Grants No. HL-30616 from the National Institutes of Health. The United States Government may retain certain rights.

FIELD OF THE INVENTION

The expanding use of fibrinolytic therapy has resulted in improved outcomes in patients with myocardial infarction and peripheral vascular disease and promise of reduced disability following stroke. These advances also focused attention on the limitations of therapy and stimulated efforts to improve effectiveness and decrease adverse effects. Thus, in patients with acute myocardial infarction, up to 20% do not achieve reperfusion, and the benefit decreases with longer periods of ischemia, emphasizing the need for rapidly acting therapy. For stroke, the need for very early treatment and serious consequences of intracranial bleeding limit application. Problems with treatment of peripheral arterial occlusion include the need for proper catheter replacement, a longer duration of treatment, and a requirement for subsequent endovascular or surgical reconstruction in most patients. Its limited use for venous thromboembolic disease reflects the high incidence of therapeutic failure and lower benefit-to-risk ratio. Efforts to overcome these obstacles have focused on development of new plasminogen activators, more effective dosing regimens, and the use of adjunctive antiplatelet and anticoagulant therapy.

The use of ultrasound represents a completely different, nonpharmacologic approach to improving fibrinolytic therapy and offers unique potential to increase reperfusion and limit bleeding complications. Several reports have shown marked acceleration of fibrinolysis using low intensity ultrasound in vitro (1–5) and in animal models (6–10). Miniaturized transducers have also been attached to catheters for endovascular use (11–13), and this offers the potential to deliver localized ultrasound at the site of thrombosis while limiting insonification of normal tissue. The choice of ultrasound frequency is critical for successful clinical application as it influences both efficacy and safety. Early studies employed frequencies of 500 kHz or greater but poor tissue penetration and unacceptable heating were limiting. These problems are less at lower frequencies, and the enhancement of thrombolysis in vitro is greater at 40 kHz than at 1 MHz (5). Even though ultrasound has some benefit, a need exists for improved methods of treating tissue with ultrasound.

The emergence of nitric oxide (NO), a reactive, inorganic radical gas as a molecule contributing to important physiological and pathological processes is one of the major biological revelations of recent times. This molecule is produced under a variety of physiological and pathological conditions by cells mediating vital biological functions. Examples include endothelial cells lining the blood vessels; nitric oxide derived from these cells relaxes smooth muscle and regulates blood pressure and has significant effects on the function of circulating blood cells such as platelets and neutrophils as well as on smooth muscle, both of the blood vessels and also of other organs such as the airways. In the brain and elsewhere nitric oxide serves as a neurotransmitter in non-adrenergic non-cholinergic neurons. In these instances nitric oxide appears to be produced in small amounts on an intermittent basis in response to various endogenous molecular signals. In the immune system nitric oxide can be synthesized in much larger amounts on a protracted basis. Its production is induced by exogenous or endogenous inflammatory stimuli, notably endotoxin and cytokines elaborated by cells of the host defense system in response to infectious and inflammatory stimuli. This induced production results in prolonged nitric oxide release which contributes both to host defense processes such as the killing of bacteria and viruses as well as pathology associated with acute and chronic inflammation in a wide variety of diseases. The discovery that nitric oxide production is mediated by a unique series of three closely related enzymes, named nitric oxide synthases, which utilize the amino acid arginine and molecular oxygen as co-substrates has provided an understanding of the biochemistry of this molecule and provides distinct pharmacological targets for the inhibition of the synthesis of this mediator, which should provide significant beneficial effects in a wide variety of diseases. Thus it is desirable to have methods for controlling NO production.

The present invention overcomes the prior limitations of ultrasound fibrinolytic therapy. In addition, the present invention provides a safe and easy method for controlling the production of NO. These methods will greatly expand the utility of ultrasound in the treatment of disease.

SUMMARY OF THE INVENTION

The present invention provides a method for improving vasodilation in ischemic tissue by applying ultrasound to the ischemic tissue under conditions effective to increase blood flow to said ischemic tissue.

In another embodiment the invention provides a method of treating tissue damage by applying ultrasound to said tissue damage under conditions effective to treat said tissue damage.

The present invention may also be used to accelerate wound healing in a patient. Again, ultrasound is applied to the wound under conditions effective to accelerate healing. This approach can be utilized to accelerate healing of various types of wounds, including ulcers and bone fractures.

The invention also provides a method for increasing nitric oxide production in tissue by applying ultrasound to the tissue.

Also within the scope of the invention is a method of treating neurodegenerative and muscle diseases. Ultrasound is applied to diseased tissue under conditions effective to increase nitric oxide production in the diseased tissue.

BRIEF DESCRIPTION OF THE DRAWINGS

FIG. 2 shows histologic changes in vessels exposed to US.

DETAILED DESCRIPTION OF THE INVENTION

Figure 1:
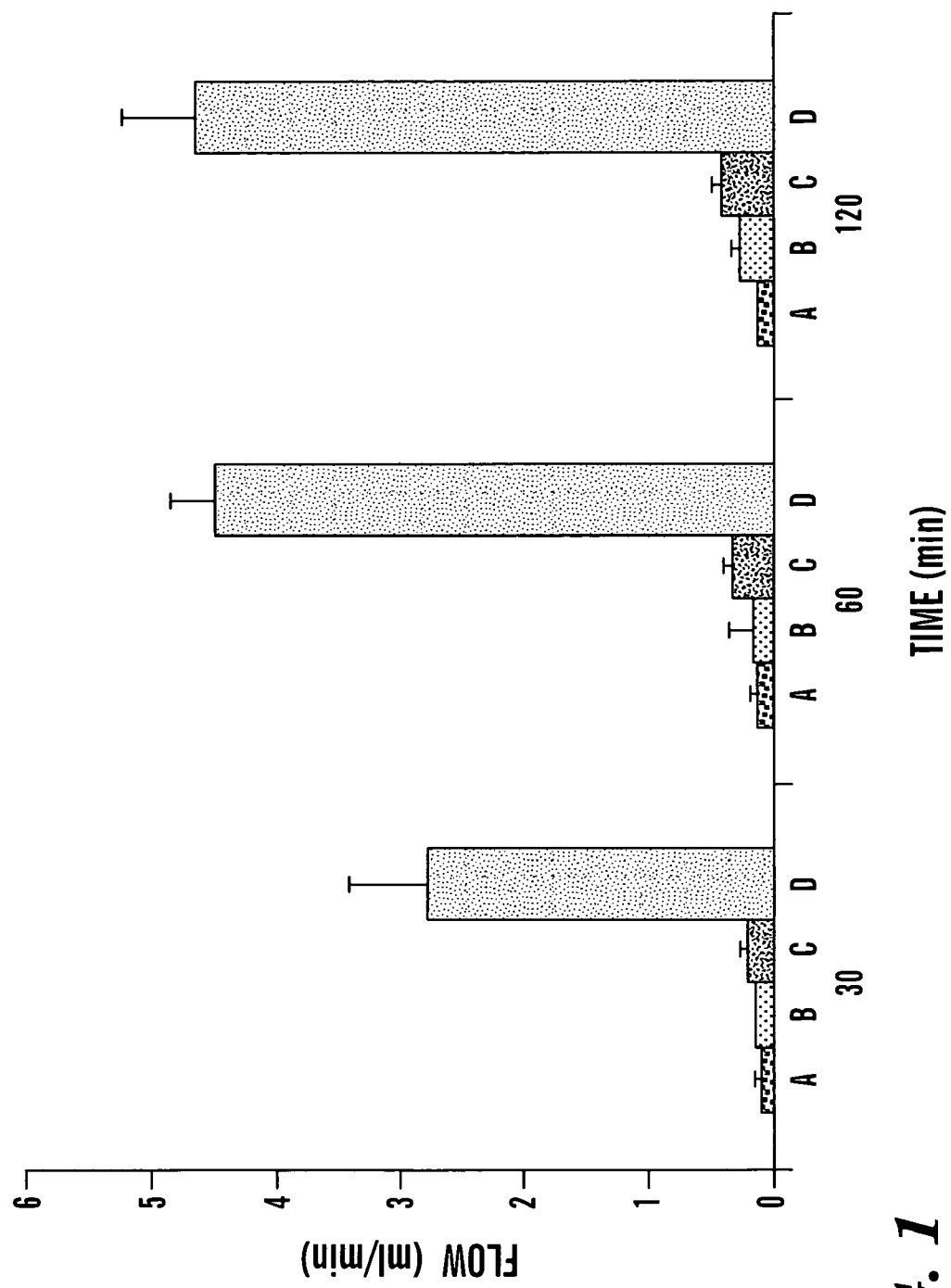
FIG. 1 demonstrates the effects of ultrasound on blood flow after femoral artery thrombolysis. Thrombi were formed by constriction of the femoral artery and external application of ferric chloride. Controls (A) received no treatment. Treatment was administered with 40 kHz ultrasound at 0.75 W/cm$^2$ (B), streptokinase administered as an intravenous bolus of 15,000 U/kg followed by an infusion of 15,000 U/kg/hr (C) or the combination of both ultrasound and streptokinase (D). Data are shown as mean±SD. There were 9, 7, 6 and 6 rabbits in groups A, B, C and D, respectively.

The present invention provides broadly applicable methods for enhancing tissue perfusion or growth and accelerating the recovery of damaged tissues using ultrasound.

Vasodilation in ischemic tissue may be improved by applying ultrasound to said ischemic tissue under conditions effective to increase blood flow to said ischemic tissue. Ultrasound has been used previously to disrupt blood clots to treat ischemia, however, the present invention provides a method for increasing vasodilation by treating the surrounding ischemic tissue with ultrasound. Such treatment results in increased vasodilation and blood flow in the tissue. This approach provides substantial benefit even when the obstruction can not be disrupted, such as a surgical severing of the blood vessel.

In a preferred embodiment of the invention ultrasound is used to treat arterial obstruction. Arterial obstruction may be acute vascular obstruction or chronic vascular obstruction. Obstruction may results from any number of internal or external factors. Examples include obstructions resulting from clots, sutures (i.e. vessels being tied off), tumors, emboli, hematomas, trauma, vasospasm, and artheroscrolosis.

In one particular embodiment, the present invention may be used to treat patients after subarachnoid hemmorages to prevent or control vasospasm.

Ultrasound may be applied to the tissue in a variety of manners. It may be applied to surgically exposed muscle. Alternatively it may be applied to skin overlying the tissue to be treated. Another approach is to place the ultrasound transmitter on a catheter which can be introduced into the area without full scale surgery.

In a preferred embodiment, the ultrasound is applied to the tissue by placing an ultrasound transducer adjacent to the tissue and then subjecting the tissue to ultrasound treatment with said ultrasound transducer. In a preferred embodiment, the ultrasound transducer operates at a frequency of from about 10 to 300 kHz. Preferably, the ultrasound transducer operates at an intensity of from about 0.25 to 2 W/cm$^2$. In a more preferred embodiment, the ultrasound transducer operates at a frequency of about 40 kHz and an intensity of about 0.75 W/cm$^2$.

The present invention also provides a method of treating tissue damage by applying ultrasound to said tissue damage under conditions effective to treat said tissue damage. Although the method is broadly applicable to damaged tissues, it is particularly suited to treating damage which is the result of a stroke, coronary artery occlusion, or peripheral arterial occlusion.

Another embodiment of the invention provides a method of accelerating wound healing in a patient. Wound healing can be accelerated by applying ultrasound to said wound under conditions effective to increase blood flow to said wound or to increase the production of nitric oxide. Although the method of the invention may be used with a wide variety of different wounds, for example, the method may be used to accelerate the healing of a bone fracture or an ischemic ulcer.

The invention also provides a method for increasing the production of nitric oxide by applying ultrasound to tissue under conditions effective to increase nitric oxide concentrations. Such an approach may be used to increase nitric oxide production to regulate vascular tone. More specifically, the method may be used to increase nitric oxide production to increase vasodilation. In a preferred embodiment, the tissue being treated is ischemic tissue.

Nitric Oxide ("NO") has been demonstrated to play a key role in a wide variety of physiological pathways (34–36). NO is a uniquely diffusible and reactive molecular messenger in the vascular and immune systems. In the peripheral nervous system, NO acts as a classical neurotransmitter in regulating gastrointestinal motility, regional blood flow, and neuroendocrine function. In the brain, NO acts as a neuromodulator to control behavioral activity, influence memory function, and intensify responses to painful stimuli. NO is not restricted to neurons. Skeletal muscle is also a major source of NO where NO regulates both metabolism and muscle contractility.

Increased NO production can modulate tissue injury. For example large amounts of NO produced during ischemia mediate neuronal injury resulting from stroke (39). NO-mediated damage may account for neurodegeneration in a number of other conditions as well, including Parkinson's disease, amyotrophic lateral sclerosis, and Huntington's disease. NO signaling is also perturbed in various muscle diseases, particularly in Duchenne muscular dystrophy, and that perturbation may contribute to the disease process.

Physiological functions for neuron-derived NO were first demonstrated in the gastrointestinal tract. Molecular biological studies have helped detail the mechanisms for NO-mediated neurotransmission. In the intestine, neuronal NOS (nNOS) is selectively concentrated in axon varicosities of myenteric neurons. Adjacent intestinal smooth muscle cells contain an "NO receptor," the soluble guanylyl cyclase. During intestinal peristalsis, myenteric neurons fire action potentials, and the resulting calcium influx activates calmodulin, which in turn stimulates nNOS. The NO then diffuses into adjacent smooth muscle cells and augments accumulation of cGMP, which mediates intestinal relaxation. Knockout mice lacking nNOS display a grossly enlarged stomach that histologically resembles the human disease hypertrophic pyloric stenosis (40). Alterations in NOS may also play a causal role in some newborns with this disorder, as recent genetic studies indicate that nNOS is a susceptibility locus for infantile pyloric stenosis (41).

Neuron-derived NO also plays a major role in regulation of blood flow. In brain, neuronal activity is associated with an increase in local blood flow, and this response is prevented by NOS inhibitors (42). Particularly high levels of nNOS occur in vasodilator nerves that innervate the large cerebral blood vessels (43). Abnormal reactivity of these vessels appears to mediate migraine headache, as sumatriptan constricts these large vessels and controls headache (44). Sumatriptan is also effective in treatment of nitroglycerin-induced headache, suggesting a role for endogenous NO in migraine. Therefore, pharmacological manipulations of nNOS may offer an avenue for migraine therapy.

Neuron-derived NO also mediates penile erection through regulation of blood flow. nNOS is enriched in neurons of the pelvic plexus and NOS inhibitors block penile erection in animal models in vivo (45) and in strips of human cavernosal tissue in vitro (46). However, nNOS mutant mice display normal erectile function (47). Apparently NO derived from other NOS isoforms compensates for the loss of nNOS, as NOS inhibitors block penile erection in nNOS mutant mice. Recent studies demonstrate that abnormalities in NO biosynthesis may also underlie erectile dysfunction. Diabetes mellitus is associated with impaired NOS-dependent erectile function (48). NOS levels in penis are also decreased in aging rats, and this age-related decrease correlates with impaired erectile responses (49). Androgens are essential for penile reflexes in the rat and are also essential for normal libido. Similarly, nNOS expression in penis is dependent upon active androgens as nNOS levels decrease by 60% 1 wk after castration but are restored to normal levels with testosterone replacement (50). Therefore, pharmacological manipulation of NO or NOS expression may offer a viable strategy for treatment for some causes of erectile dysfunction.

Because NO is a uniquely diffusible mediator, it was proposed on theoretical grounds that NO may mediate neuronal plasticity, which underlies aspects of both development and information storage in brain. Evidence for NO involvement in synaptic plasticity has accumulated steadily. At the cellular level, NO signaling appears to be essential for two forms of neuronal plasticity: long-term potentiation (LTP) in the hippocampus (51) and long-term depression in the cerebellum (52). In these cellular models, repeated neuronal stimulation yields long-lasting changes in synaptic strength. NOS inhibitors prevent these changes. Studies with NOS inhibitors have been controversial because these arginine analogues often have nonspecific effects. This controversy may now be resolved by studies of NOS knockout mice. Both endothelial NOS (eNOS) and nNOS activities are found in hippocampus. Mice that either lack eNOS or nNOS have essentially normal LTP, whereas mutant mice deficient in both eNOS and nNOS have substantially decreased LTP (53).

Although endogenous NO was originally appreciated as a mediator of smooth muscle relaxation, more recent studies indicate a role for NO in skeletal muscle as well. nNOS mRNA is expressed at high levels in human skeletal muscle (37), where it is alternatively spliced, yielding a muscle-specific isoform (nNOSmicro) (54). Understanding functions for nNOS in skeletal muscle has been facilitated by the discrete localization of nNOS in myofibers. In rodent muscle, nNOS is specifically enriched beneath the sarcolemma of fast twitch muscle fibers (38). NOS activity stimulated during muscle membrane depolarization inhibits contractile force in fast twitch fibers.

In addition to modulating contractile force, NO derived from sarcolemmal nNOS regulates physiologic functions at the muscle membrane. During muscle development, myocytes fuse to form muscle myotubes, and this membrane fusion is blunted by NOS inhibitors (55). In myocyte/motor neuron co-cultures, NOS produced at the postsynaptic muscle membrane functions as a retrograde messenger to regulate myotube innervation (56). In mature muscle fibers, NOS regulates glucose uptake across the sarcolemma. Glucose uptake in skeletal muscle is regulated by both acute exercise and by insulin. NOS inhibitors selectively blunt exercise-induced uptake but have no effect on insulin-stimulated glucose transport (57). Interestingly, chronic exercise increases nNOS protein expression in muscle and this has long-lasting enhancing effects on glucose transport in heavily used muscle (57).

Since NO plays an important role in neurodegenerative and muscle diseases, the present invention can be used to treat neurodegenerative and muscle diseases by applying ultrasound to diseased tissue under conditions effective to increase nitric oxide production in the diseased tissue.

EXAMPLES

Example 1

Materials and Methods

Animal Preparation: Rabbits were anesthetized with ketamine (60 mg/kg), xylazine (6 mg/kg) and chlorpromazine (25 mg/kg), and sedation was maintained with sodium pentobarbital as needed. The femoral arteries were dissected 5 cm distal to the origin of the superficial branch, and the profunda femorus and superficial arteries were ligated close to their origin. A Doppler flow probe was placed distally around the isolated segment and two parallel ligatures were placed around the femoral artery 1 cm distal to the profunda branch. These reduced flow by approximately 50% remained in place for the duration of the experiment. Following this, of filter paper saturated with 20% ferric chloride was placed on the femoral artery and thrombosis was assessed by monitoring flow which approached 0 after occlusion. In some animals a completely occlusive suture was placed around the artery.

Experimental Protocol: Rabbits were assigned to receive: 1) ultrasound alone, 2) streptokinase alone, 3) both ultrasound and streptokinase, or 4) no treatment. There were 7, 6, 6 and 9 rabbits in groups 1, 2, 3 and 4, respectively. The source of ultrasound was a 3.5 cm diameter probe with a 1 cm diameter transducer driven in continuous mode at 0.75 W/cm$^2$, and acoustic pressures were measured before and after each experiment with a hydrophone. A balloon filled with water at 37° C. was placed over the thrombosed segment for temperature control and ultrasound transduction. The interface between the balloon and the artery was covered by a layer of ultrasound transmission gel. Streptokinase was administered as an intravenous bolus of 15,000 U/kg followed by an infusion of 15,000 U/kg/hr for two hours. This dose was selected because our prior experience with this model indicated that it was relatively ineffective alone, that 1 MHz ultrasound enhanced its effects (18) and data in vitro indicated that 40 kHz had a greater effect on thrombolysis than 1 MHz ultrasound (14). The pH of the muscle was also monitored using a pH meter (Model HI-9023C, Hanna Instruments, Woonsocket, R.I.). Perfusion in the gracilis muscle was measured using a laser-Doppler flow meter (BFL 21 Transonic Systems) with an output in units (TPU) that is linearly related to the number of red cells times their velocity in the hemispheric measuring volume (26–28). The measuring surface was 1 mm$^2$, and the light penetration depth was approximately 1 mm.

Temperature monitoring in four rabbits was performed with a copper-constantin fine wire thermocouple placed under the femoral artery or on the exposed surface of the femur and connected to a temperature gauge. To assess the effects of heating on tissue perfusion, a balloon containing water at 32° C. to 42° C. was laid over the gracilis muscle. At the completion of each experiment, animals were euthanized and samples for histology were excised and fixed in 10% buffered formalin. Specimens were processed in paraffin, sectioned at 4 microns, and stained with hematoxylin and eosin. The stained sections were encoded to obscure treatment, and examined by an observer (RBB) blinded as to code and particular attention was paid to the endothelial cells.

Statistical Methods: The three primary outcome measures that were used to assess the effect of ultrasound were flow intensity, TPU and pH. The mixed linear model was used for statistical analysis of each of the primary measures. The responses were grouped into clusters by the individual animal (random effect) and were treated as repeated measurements taken over time and/or at different distances. Based on these models, the least square means, their standard errors and covariances were calculated, and the adjusted differences between treatment means at different time points were obtained. They were used for testing for treatment effect as well as for effect sizes for each level of grouping variables.

Example 2

Treatment of Surgically Induced Arterial Occlusion with Ultrasound

Occlusive thrombi formed in all femoral arteries within 20–30 min of placement of the constriction and application of 20% ferric chloride. Arterial flow was 12.0±0.7 ml/min at baseline, declined to 5.8±0.4 after placement of the constriction and was 0.1±0.1 after thrombosis. Three different treatment regimens were administered following thrombosis: ultrasound alone, streptokinase alone or the combination of streptokinase and US. Flow in control vessels receiving no treatment remained at near 0 after 30, 60, and 120 min (FIG. 1). Treatment with ultrasound alone resulted in no significant increase in flow, whereas treatment with streptokinase alone resulted in a small but significantly increased flow at 120 min to 0.4±0.1 ml/min (p<0.001). The combination of streptokinase and ultrasound resulted in greater reperfusion, with flow of 2.6±0.7 ml/min at 30 min, 4.6±0.4 ml/min at 60 min and 4.8±0.6 ml/min at 120 min. The 120 minute flow represented 83% of the flow of 5.8±0.4 ml/min after placement of the external constrictor but prior to thrombosis. These results indicate that the application of ultrasound markedly accelerates arterial reperfusion as compared with streptokinase alone and that ultrasound by itself had no appreciable effect.

Example 3

Monitoring of Heating by Ultrasound

Figure 2A:
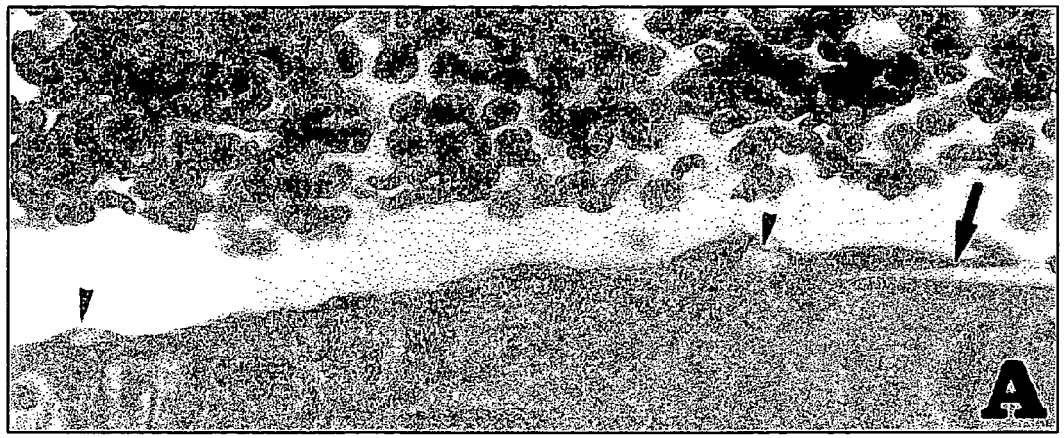
FIG. 2A shows vessel walls with endothelial cells showing occasional cytoplasmic vacuoles (arrowheads) and lifting of a single endothelial cell (arrow).
Figure 2B:
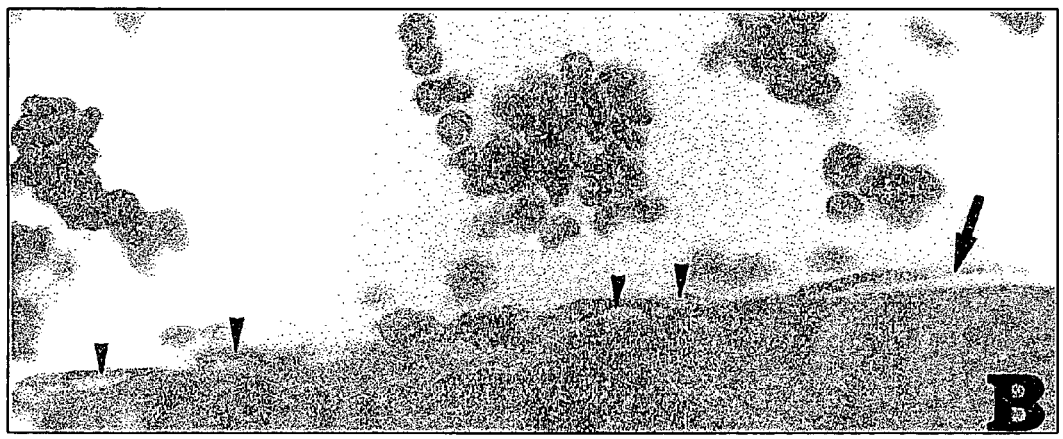
FIG. 2B shows a Segment of treated artery with all endothelial cells showing cytoplasmic vacuoles (arrowheads), and some rounding up with lifting (arrow).
Figure 2C:
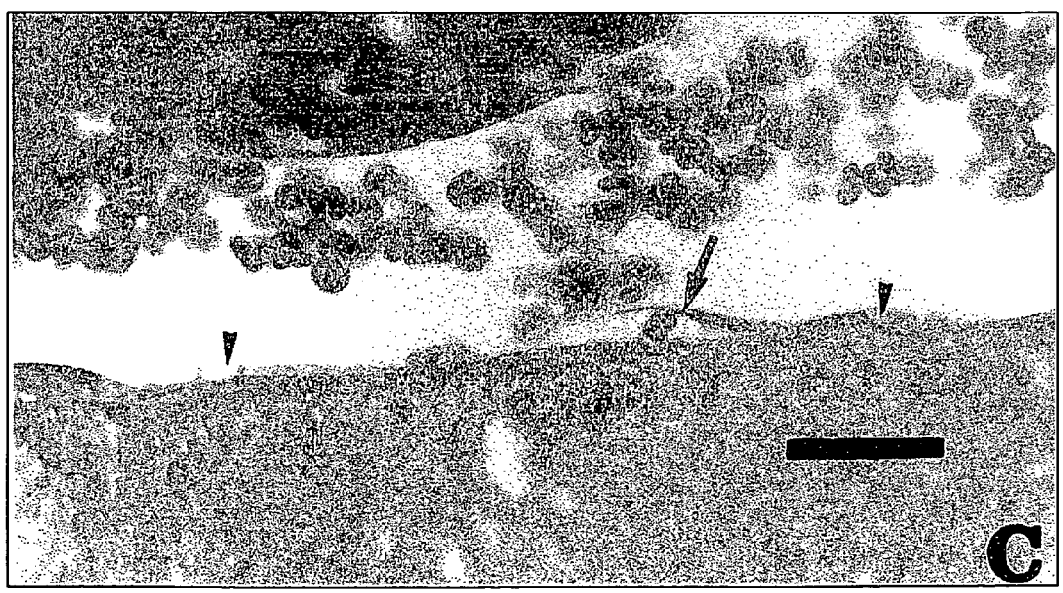
FIG. 2C shows a segment of artery with vacuolization (arrowheads) and complete lifting of an endothelial cell (arrow) with erythrocytes under the lifted endothelial cell in contact with basement membrane. Bar=20 micrometers.

US application can cause heating, and temperature was monitored using a thermocouple placed adjacent to the thrombosed vessel or at the surface of the femur. With application of ultrasound the average initial temperature increase at the femoral artery was 0.02° C./min, and it was 0.04° C./min at the surface of the femur. The maximum temperature increase after 60 min was 1.6±1.3° C. at the femoral artery and 1.1±0.7° C. at the femur. Histologically, examination showed that vessels exposed to US, regardless of other treatment components (streptokinase, ligation, clot), had a pronounced tendency for endothelial cell vacuolization, and some cells lifted up off the underlying basement membrane (FIG. 2). Occasionally, erythrocytes were seen in direct contact with the basement membrane.

Example 4

Capillary Perfusion after Ultrasound Treatment

Figure 3:
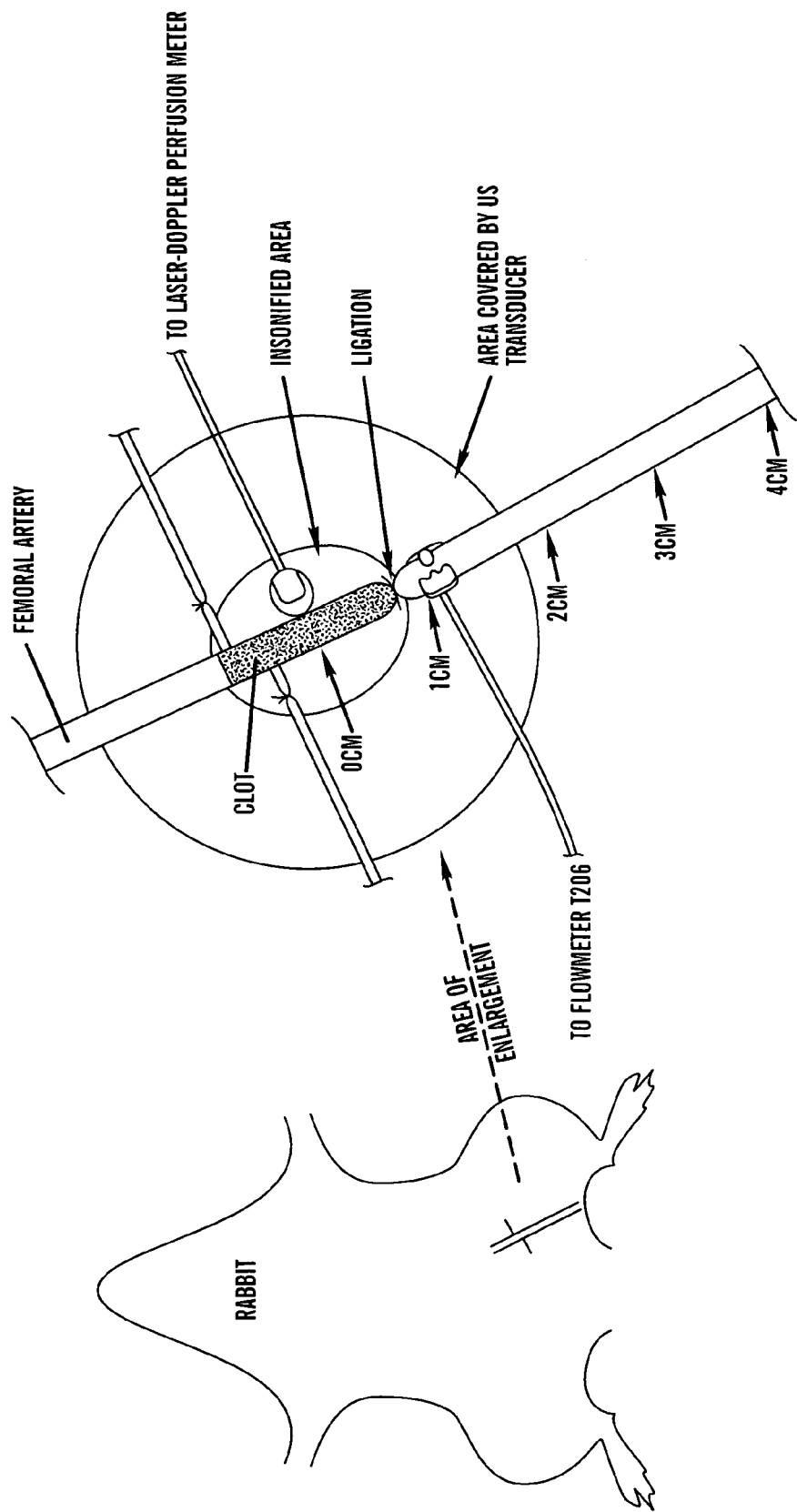
FIG. 3 is a schematic drawing of the experimental site.
Figure 4A:
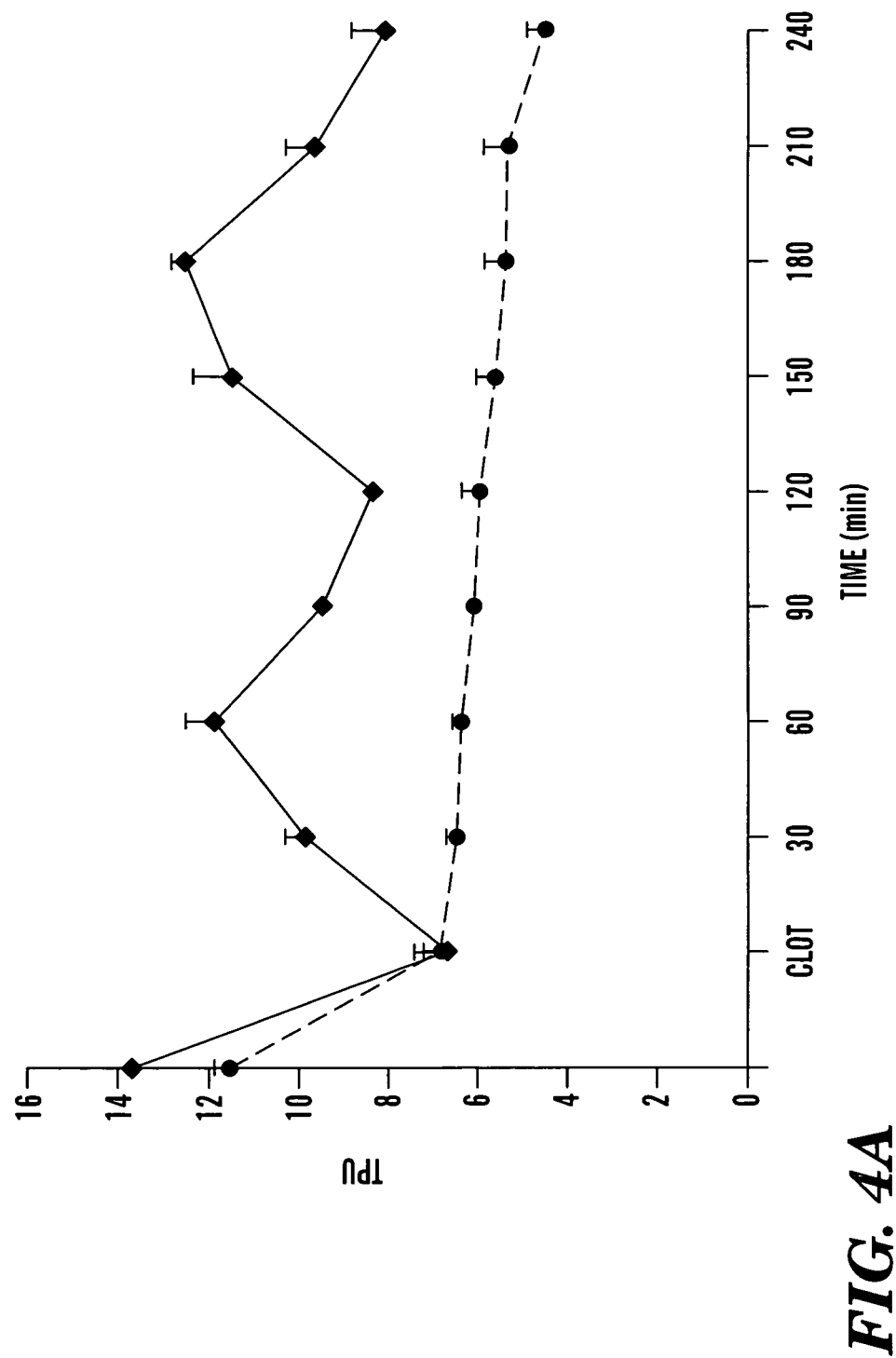
FIG. 4 shows the effects of ultrasound on tissue perfusion and pH. For FIG. 4A, perfusion was measured using a laser-Doppler probe placed over the gracilus muscle near the center of the transducer. In control animals (dotted line) perfusion was reduced after clot formation and declined further over the period of observation. The nine animals receiving 40 kHz ultrasound at 0.75 W/cm$^2$ (solid line) demonstrated increased perfusion until 60 min when the ultrasound transducer was turned off. Ultrasound was applied again between 120 min and 180 min and then turned off again. For FIG. 4B, the same protocol was followed using an electrode to measure muscle pH.

During these experiments, it was observed that muscle adjacent to the femoral artery lost its normal pink, vital color soon after thrombosis and became a brownish-purple. Application of ultrasound restored the normal pink color even when no thrombolysis occurred and femoral artery flow remained near zero. Therefore, perfusion in the gracilis muscle was characterized using a probe which is sensitive to capillary blood flow (FIG. 3). In control experiments, tissue perfusion was stable for periods up to 60 min indicating that application of the unactivated probe by itself did not tissue perfusion. At baseline, prior to vessel constriction or thrombosis, capillary perfusion was 13.7±0.4 U (FIG. 4A). This declined to 6.8±0.4 U immediately after thrombosis and then declined progressively to 4.5±0.4 U after 240 min in animals receiving no treatment. The application of ultrasound resulted in a significant increase in perfusion to 10.0±0.5 U at 30 min and a further increase to 12.1±0.5 U at 60 min (p<0.001 for both). To determine if the effect of ultrasound was reversible, the transducer was switched off at 60 min, and perfusion then declined progressively to 9.7±0.2 U at 90 min and to 8.5±0.2 U at 120 min (p<0.001 for both in comparison with 60 min). At 120 min the transducer was reactivated, and this resulted again in improved perfusion to 11.8±0.8 U at 150 min and 12.7±0.4 U at 180 min (p<0.001 for both in comparison with 120 min). When the transducer was switched off at 180 min, perfusion again declined and reached 8.2±0.8 U at 240 min. The Doppler flow probe placed distally on the artery showed no flow for the duration of the experiment. The same changes were observed when the vessel was ligated completely with sutures to preclude any change in femoral artery flow. Because tissue perfusion is sensitive to temperature, experiments were carried out to determine whether US-induced heating could explain the changes. Muscle was heated from 32° C. to 42° C. using warm water in a balloon and TPU increased from 6.2 to 7.2 U over this temperature range. Since the maximum temperature increase with ultrasound was less than 2° C., heating alone could not account for the US-induced increase in perfusion in the ischemic area.

Example 5

Metabolism and Acidosis in Ultrasound Treated Ischemic Muscle

Figure 4B:
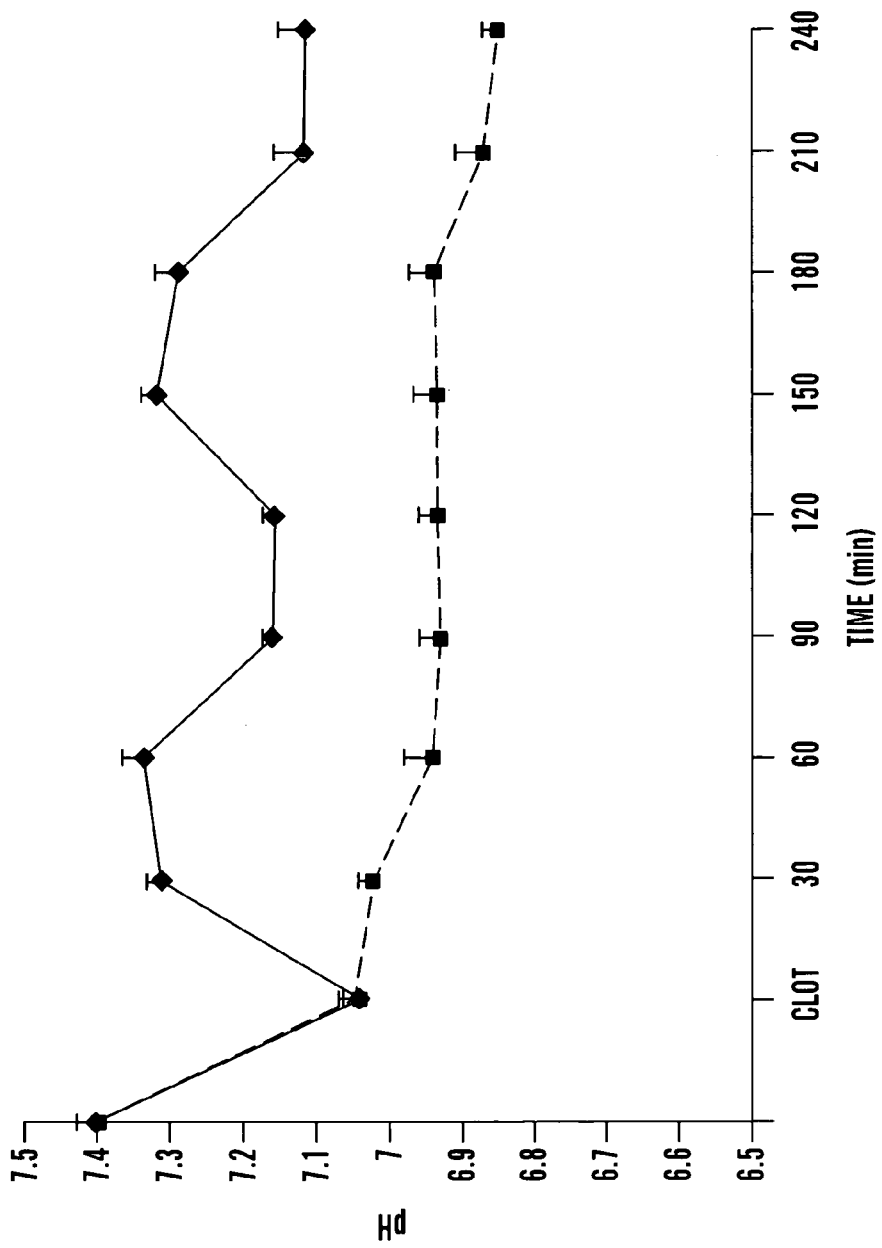

The increased tissue perfusion following application of ultrasound appeared to improve the metabolism of ischemic muscle and ameliorate acidosis, and this was investigated with a similar experimental design using a pH probe (FIG. 4B). Following surgical exposure but prior thrombosis, the baseline muscle pH was 7.41±0.02, but this declined to 7.05±0.02 after thrombotic occlusion. In the absence of treatment, pH declined slowly but progressively to reach 6.86±0.02 at 240 min. The application of ultrasound reversed the acidosis, and muscle pH increased significantly to 7.31±0.02 after 30 min and to 7.34±0.03 following 60 min (p<0.001 for both). At 60 min the ultrasound was turned off, and muscle pH declined to 7.17±0.01 at 90 min and then showed little change to 7.16±0.02 at 120 min. The transducer was then turned on, and pH again improved to 7.32±0.02 at 150 min and 7.30±0.03 at 180 min. At this time the transducer was again turned off, and pH declined to 7.13±0.04 at 210 min. The differences between means were all significant (p<0.001).

Figure 5A:
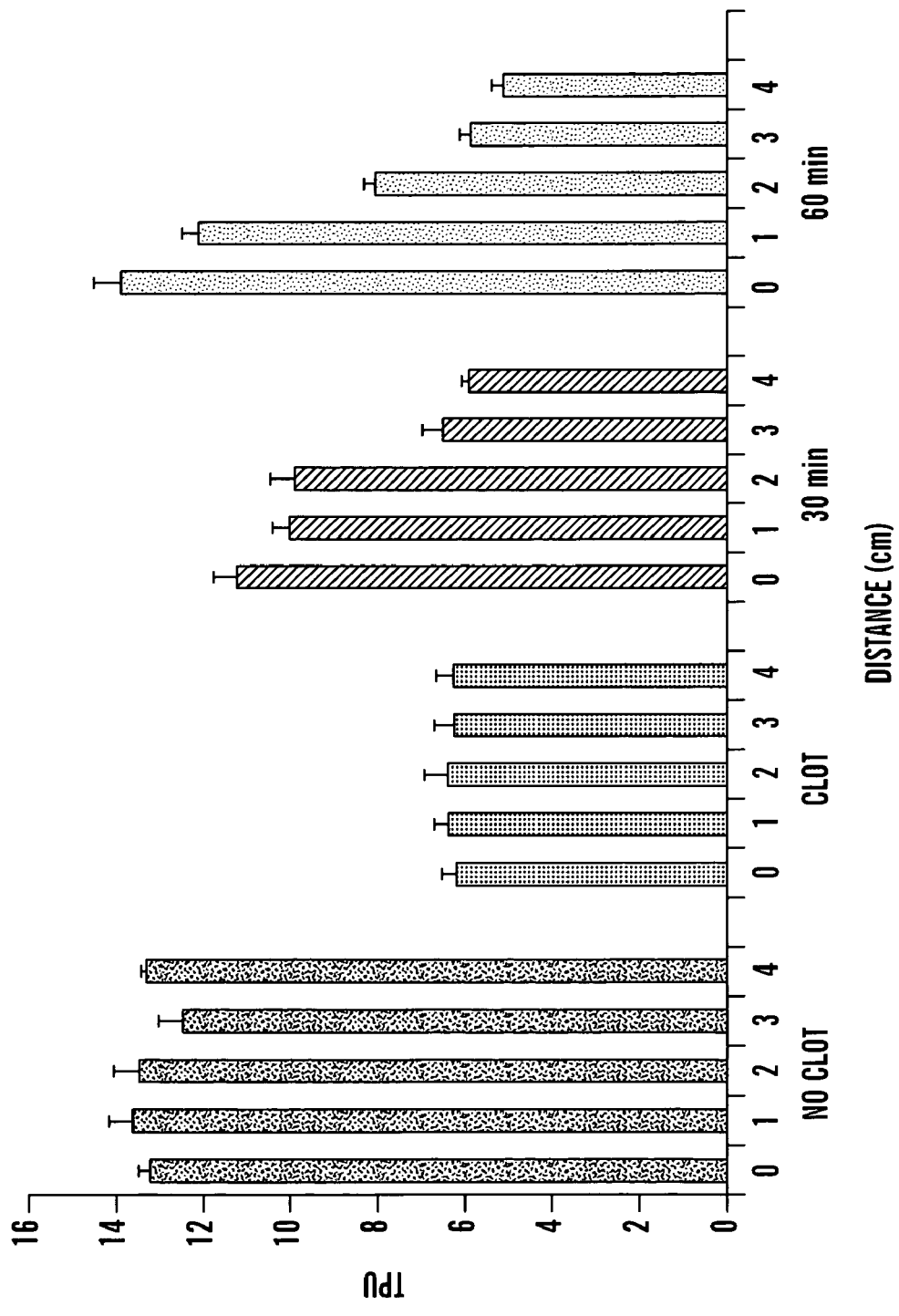
In FIG. 5A tissue perfusion was measured in five rabbits by placing the probe near the center of the transducer (0 cm) or 1, 2, 3, or 4 cm distally. In control limbs (no clot), there was no external constriction or thrombosis. Following formation of a clot, tissue perfusion was reduced. 40 kHz ultrasound at 0.75 W/cm$^2$ was then applied for 30 or 60 min. The diameter of the insonified area was 1 cm (FIG. 3) The same protocol was used with measurement of tissue pH in five additional rabbits (FIG. 5B). No thrombolytic therapy was given, and there was no flow in the femoral artery throughout the experiment. Data are mean±SD.

To determine whether the effect of ultrasound on tissue perfusion and pH was limited to the insonified tissue, measurements were made at multiple locations laterally and distally during insonification (FIG. 5A). Perfusion measured from the center of the transducer to 4 cm distally at baseline was between 12.4 and 13.6 U, and after thrombosis it decreased to between 6.3 and 6.5 U. Perfusion measurements were then made after application of ultrasound for 30 and 60 min. At 0 cm (FIG. 5A), perfusion increased to 11.1±0.5 U at 30 min and further to 14.0±0.6 U at 60 min. The effect declined at sites distal from the center of the transducer. This was most evident at 60 min with values of 12.1±0.4, 8.3±0.3, 6.0±0.3 and 5.3±0.3 at 1, 2, 3, and 4 cm, respectively. The readings at 3 and 4 cm were the same as those in control animals not exposed to US. Since the diameter of the transducer was 1 cm, these findings suggest that the ultrasound effect is limited to the insonified tissue. In other experiments, the transducer was applied at sites 1, 2, 3 and 4 cm distally. Insonification at these sites resulted in normalization of TPU, indicating that the effect could be induced at these sites, but required direct ultrasound exposure.

Figure 5B:
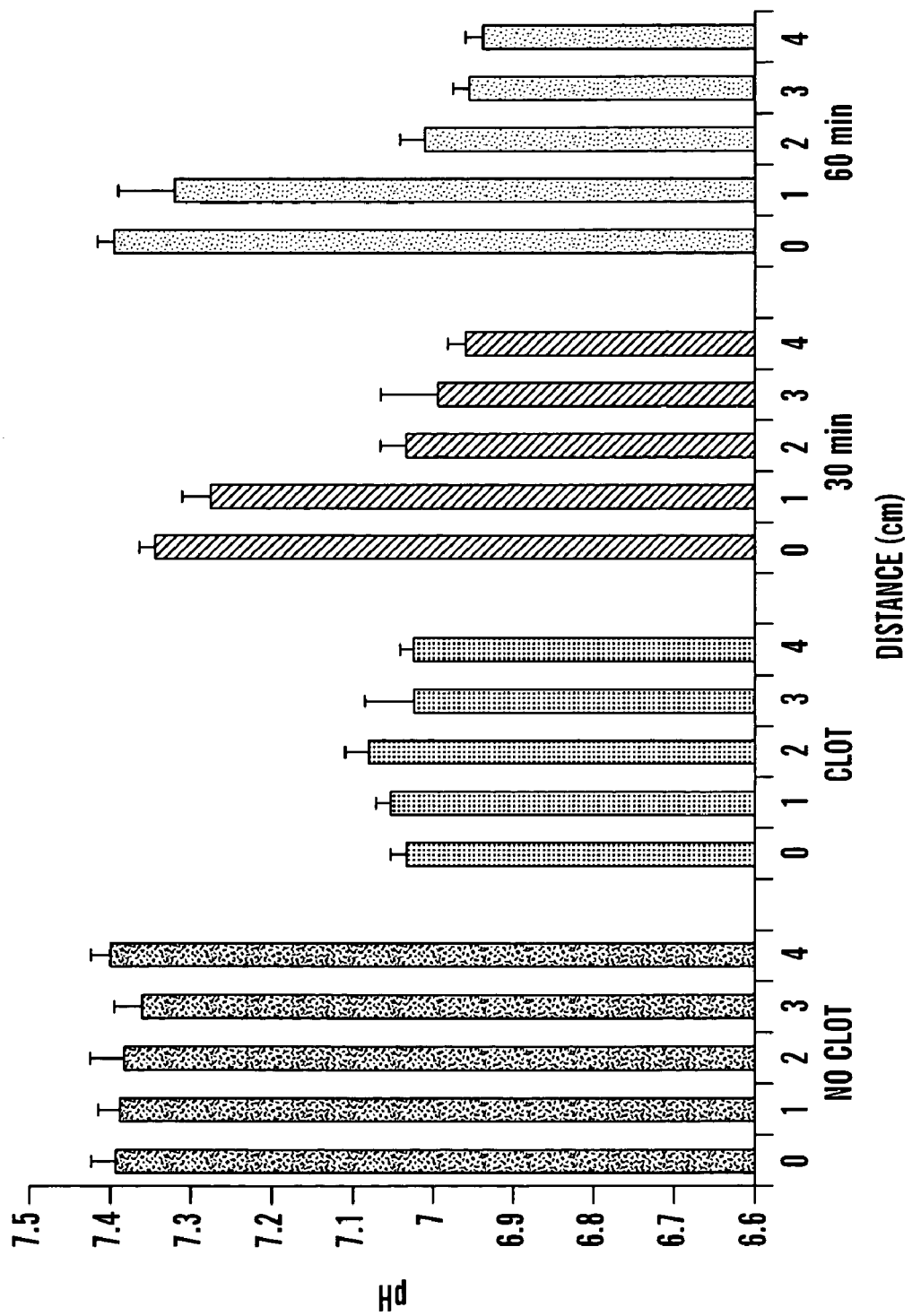
FIG. 5 shows the regional distribution of tissue perfusion and pH in relation to the location of the ultrasound transducer.

Similar experiments were performed measuring muscle pH (FIG. 5B). At baseline and before thrombosis, muscle pH was between 7.36 and 7.42 within the 4 cm area. This declined to between 7.03 and 7.08 after thrombus formation. Ultrasound application improved tissue pH at the center of the transducer to 7.34 ±0.04 at 30 min and to 7.39±0.07 units at 60 min. As with perfusion (FIG. 5A), the effect was limited to the insonified area, and muscle pH at 3 and 4 cm was not improved during insonification.

Example 6

Investigation of the Role of Nitric Oxide

Nitric oxide is an important regulator of vascular tone, and its synthesis can be affected by mechanical stresses such as alterations in flow. Therefore, it was hypothesized that ultrasound may improve tissue perfusion and pH in ischemic tissue by effecting nitric oxide production. To test this hypothesis, experiments were repeated in the rabbit femoral artery thrombosis model to document the effect of ultrasound on acidosis and tissue perfusion. An inhibitor of nitric oxide production, N-Nitro-L-arginine methyl esther hydrochloride (NAMA) was incorporated into the experiments.

Methods: The rabbit femoral artery thrombosis/ligation method as described above was used. 40 kHz ultrasound was applied at 0.75 W/cm2 in selected limbs and omitted in controls. In some animals L-NAMA was injected in a bolus of 50 mg/kg 30 minutes before occlusion of the femoral artery. Controls received no NAMA. Measurements of tissue perfusion using a laser Doppler probe and of muscle pH were performed as described previously.

Figure 6A:
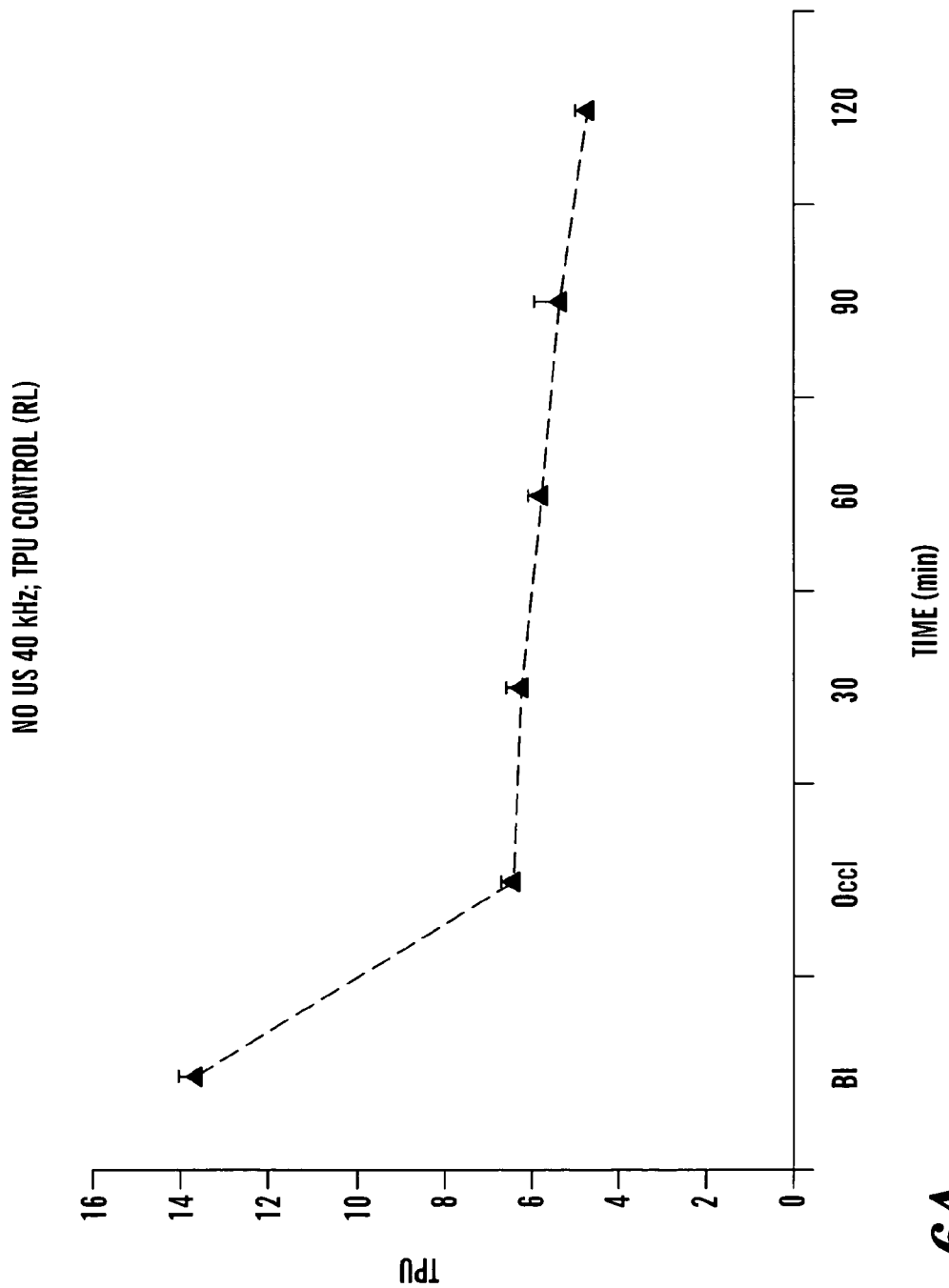
FIGS. 6A and 6B the effect on tissue perfusion and pH after the right femoral artery was ligated causing total occlusion (occl). TPU was measured with a laser Doppler probe and pH with a sensitive surface electrode. Over the duration of the two hour experiment the tissue perfusion and pH remained stable or declined slightly.
Figure 6B:
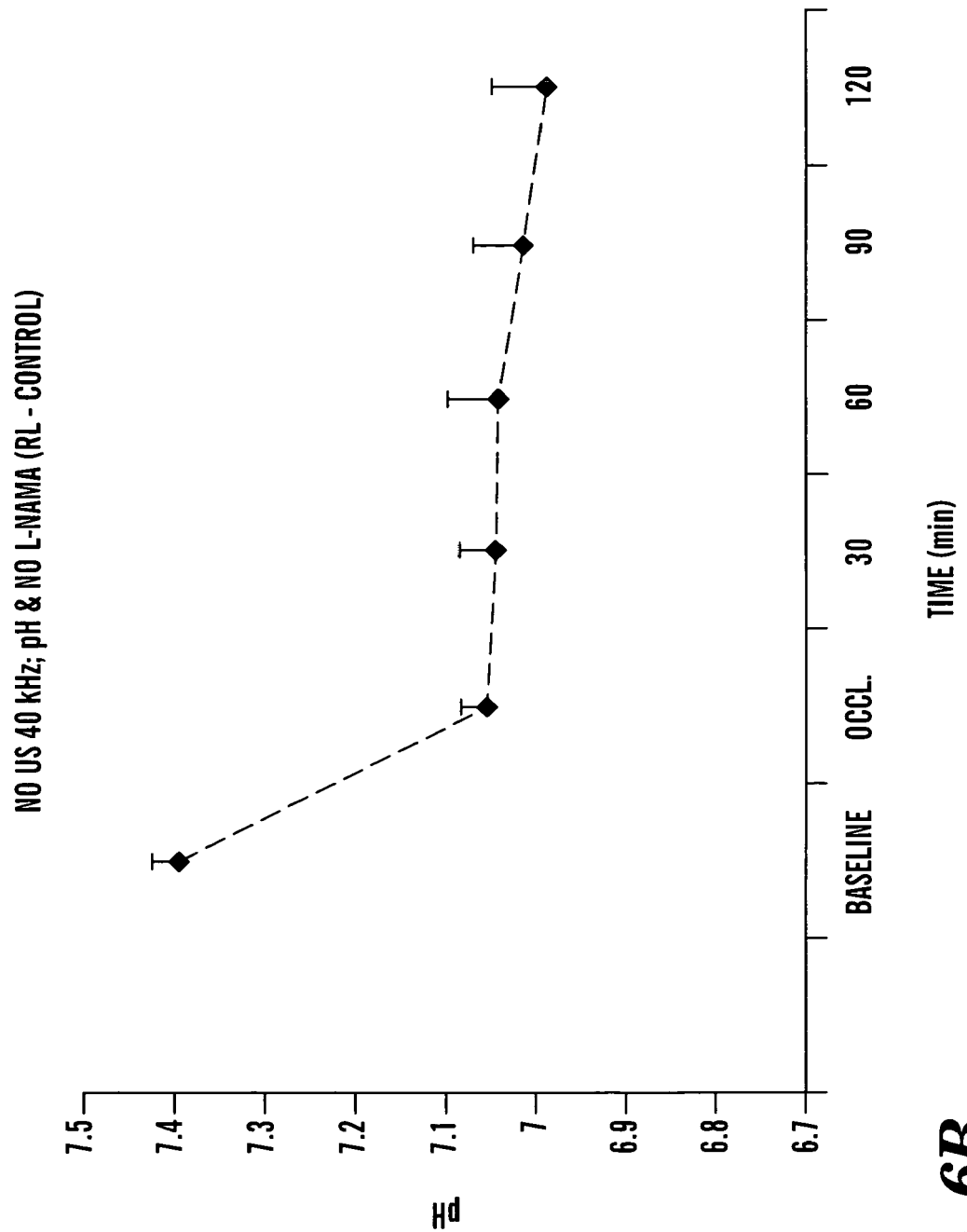
Figure 7A:
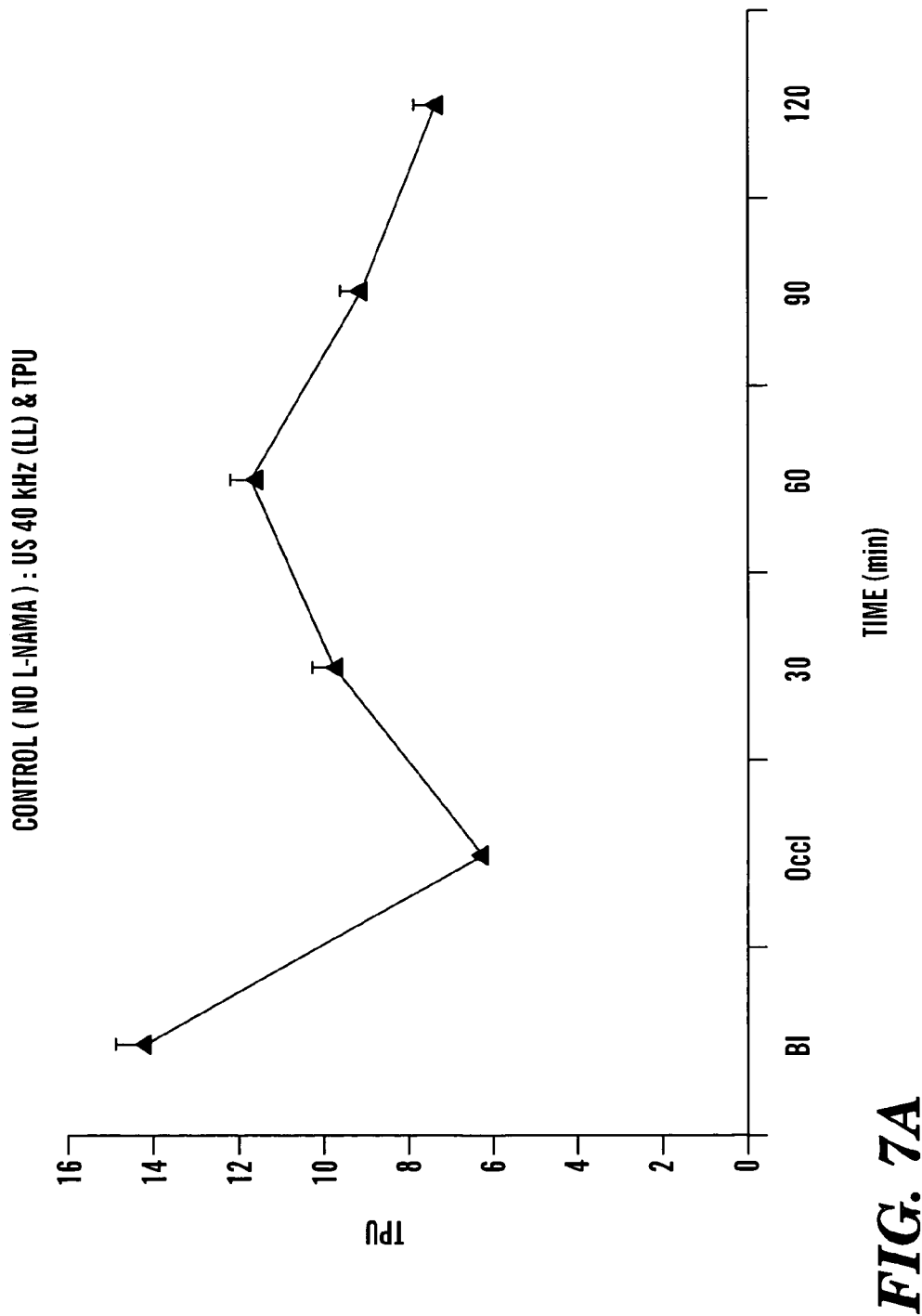
FIGS. 7A and 7B show the effects of ultrasound on tissue perfusion and pH in the ischemic rabbit leg 'Following' ligation and occlusion of the femoral artery, tissue perfusion and pH declined. Application of 40 kHz ultrasound at 0.75 W/cm2 was then commenced and continued for 60 minutes. Over this time, tissue perfusion improved (maximum effect at 60 minutes) and pH increased during the duration of ultrasound exposure from 30 minutes to 90 minutes to over 7.3. After discontinuation of US, both tissue perfusion and pH declined.
Figure 7B:
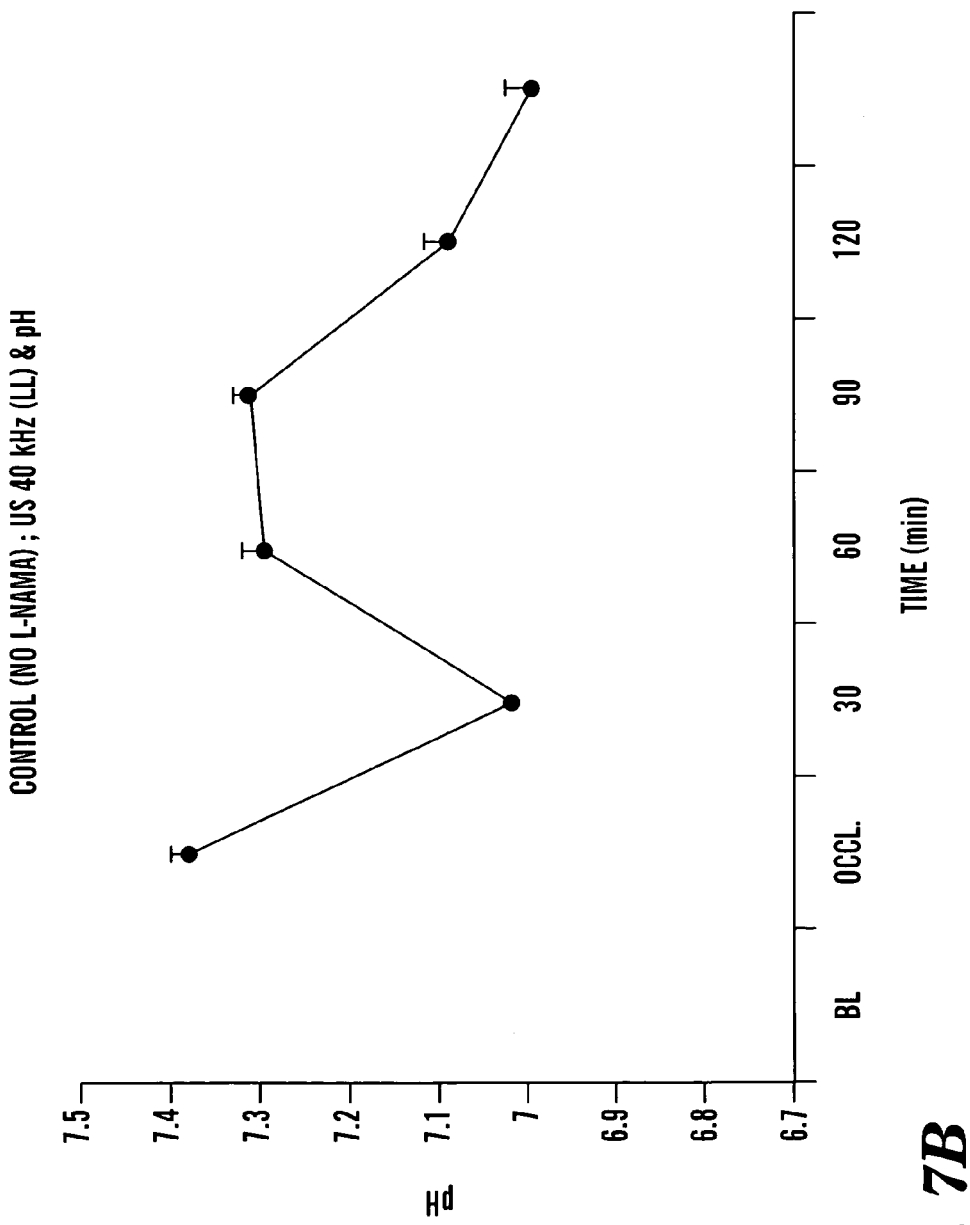
Figure 8A:
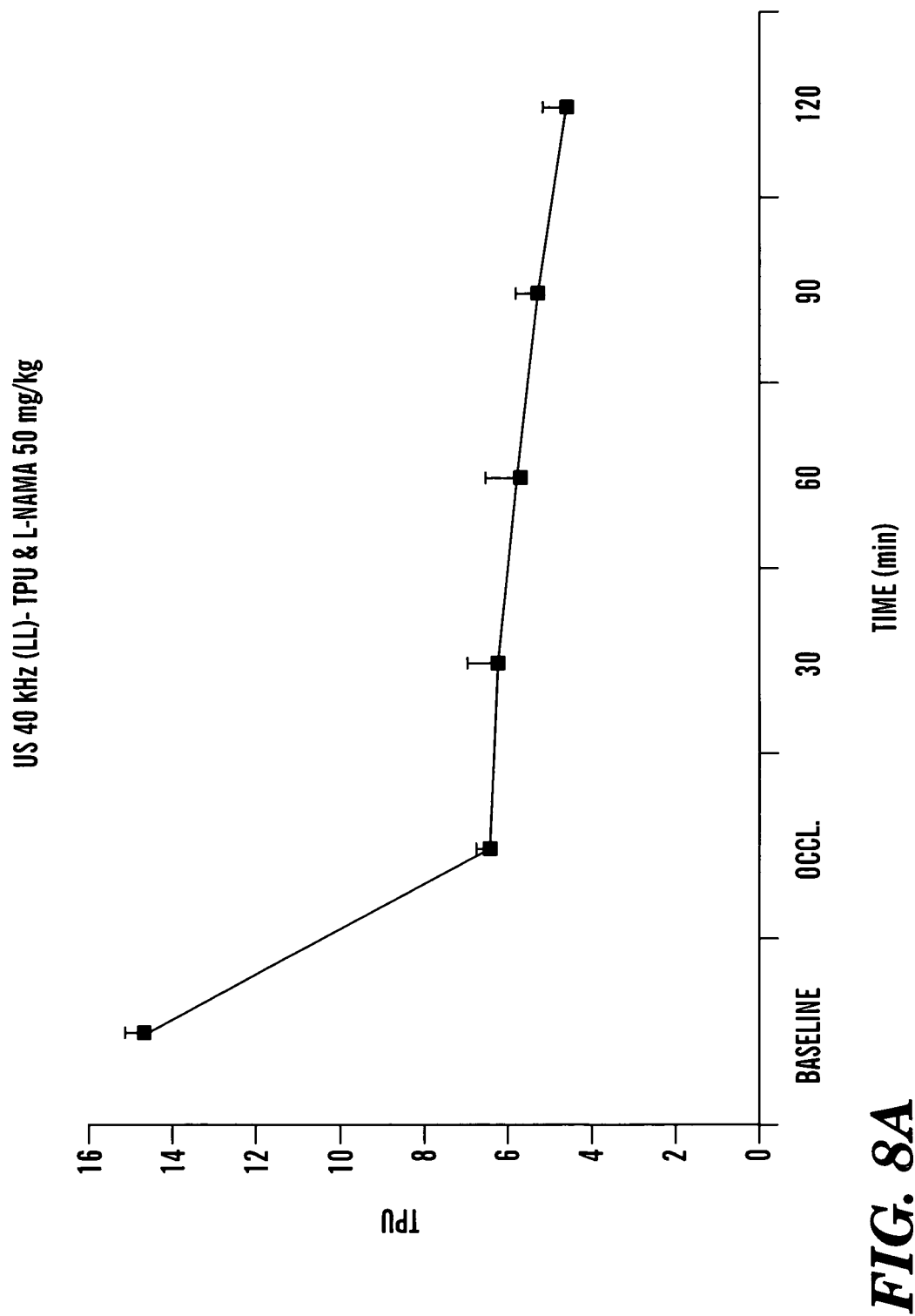
FIGS. 8A and 8B show the effect of the nitric oxide inhibitor L-NAMA on ultrasound induced changes in pH and tissue perfusion. The experiments in FIGS. 3 and 4 were repeated, but in animals that had been pretreated with L-NAMA. Ultrasound was applied for one hour following vessel occlusion. No change in pH or TPU was observed.
Figure 8B:
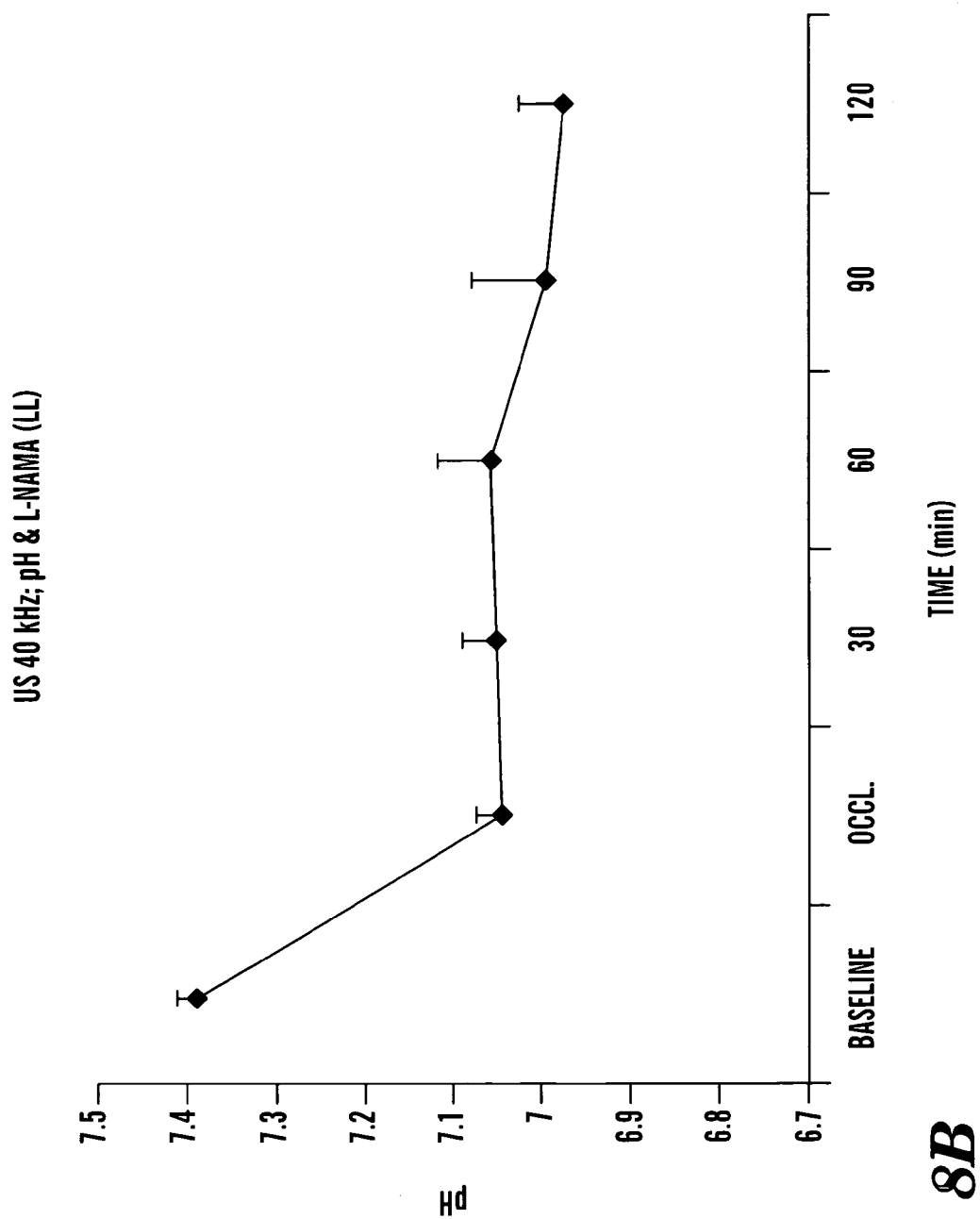

In control animals receiving no ultrasound tissue perfusion (FIG. 6A) and pH (FIG. 6B) declined after occlusion of the femoral artery and remained low for the duration of the experiment. Application of 40 kHz ultrasound at 0.75 W/cm2 resulted in improvement in tissue perfusion (FIG. 7A) and pH (FIG. 7B) as noted previously. The effect was reversible after ultrasound was discontinued in those experiments. After administration of NAMA the effect of ultrasound on TPU (FIG. 8A) and pH (FIG. 8B) was eliminated and perfusion and pH remained low or declined for the duration of the experiment, similar to the findings in the control animals (FIGS. 6A and 6B). The administration of L-NAMA alone resulted in no change in control experiments in the absence of US.

The results confirm and extend the previous findings examining the effects of 40 kHz ultrasound on tissue perfusion and pH in the rabbit ischemic leg model. Application of 40 kHz ultrasound at 0.75 W/cm2 improved tissue perfusion and pH in the grasilus muscle. Pretreatment of the animals with L-NAMA, a selective nitric oxide inhibitor, completely aggregated the effects of US, and the animals behaved as controls in the absence of US. These findings indicate that the beneficial effect of ultrasound on tissue perfusion and pH requires an intact nitric oxide system.

Femoral artery thrombosis results in distal muscle ischemia and metabolic changes including acidosis. In the experiments reported, muscle perfusion was measured using a probe sensitive to movement of red blood cells to a depth of approximately 1 mm in the regional microcirculation (31). Unexpectedly, the application of ultrasound improved tissue perfusion, and this resulted in reversal of acidosis. Although the laser-Doppler measurement is limited to 1 mm in depth, the prolonged duration of the ultrasound effect accompanied by normalization of tissue pH and muscle color suggest that it was more general. This occurred without clot lysis and was observed even when the vessel was completely ligated, indicating that reperfusion with flow through the femoral artery was not the explanation. The improved perfusion was reversible, and the effect was limited to the insonified area with no discernable increase in perfusion either distally or laterally. The proximal leg muscles receive their primary blood supply from the femoral artery, and occlusion reduced perfusion to approximately 50% of baseline, but the residual perfusion following occlusion indicates that an alternate arterial supply provided collateral flow. The US-induced increase in perfusion in the absence of femoral artery flow suggests that arterial supply through these collateral vessels increased.

The mechanism of improved perfusion is unclear, but redistribution of collateral flow into the ischemic area may be modulated by neural or hormonal influences. Humbral mediators of vasomotor tone-include endothelin, prostacyclin, and nitric oxide. The local secretion of nitric oxide is regulated by nitric oxide synthase, an enzyme which can be induced by mechanical stress on endothelial cells (32,33) that could result from US. Thus, we hypothesize that nitric oxide-induced redistribution of flow may account for the effects of US, but further studies will be required to elucidate the physiologic mechanisms. Therapeutic application will require careful attention to limiting application of ultrasound only to ischemic tissue as inappropriate insonification to adjacent non-ischemic tissues could result in redistribution of flow away from ischemic tissue, thereby extending ischemia.

The increased tissue perfusion resulting from ultrasound has the potential to improve clinical outcomes. Rapid reversal of tissue ischemia is essential in preventing myocardial necrosis and particularly neuronal loss with stroke. This could be achieved through either removal of the arterial obstruction or by an increase flow to the ischemic area through collateral vessels. The augmentation of collateral flow offers a new approach to increasing perfusion of ischemic tissue and limiting dysfunction and necrosis.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

REFERENCES CITED

The following references which were cited herein, are hereby incorporated by reference into this application:

1. Lauer C G, Burge R, Tang D B, Bass B G, Gomez E R, Alving B M. Effect of US on tissue-type plasminogen activator-induced thrombolysis. *Circulation.* 1992; 86:1257–1264.
2. Francis C W, Onundarson P T, Carstensen E L, Blinc A, Meltzer R S. Enhancement of fibrinolysis in vitro by US. *J Clin Invest.* 1992; 90:2063–2068.
3. Luo H, Steffen W, Cercek B, Arunasalam S, Maurer G, Siegel R J. Enhancement of thrombolysis by external US. *Am Heart J.* 1993; 1125:1564–1569.
4. Tachibana K. Enhancement of fibrinolysis with US energy. *J Vasc Interv Radiol.* 1992; 3:299–303.
5. Suchkova V, Siddiqi F N, Carstensen E L, Dalecki D, Child S, Francis C W. Enhancement of fibrinolysis with 40-kHz US. *Circulation.* 1998; 98: 1030–1035.
6. Hamano K. Thrombolysis enhanced by transcutaneous ultrasonic irradiation. *Tokyo Jikekai Med J.* 1991; 106: 533–542.
7. Kornowski R, Meltzer R S, Chernine A, Vered Z, Battler A. Does external US accelerate thrombolysis? Results from a rabbit model. Circulation. 1994; 89:339–344.
8. Riggs P N, Francis C W, Bartos R S, Penney D P. US enhancement of rabbit femoral artery thrombolysis. *Cardiovasc Surg.* 1997; 5:201–207.
9. Luo H, Nishioka T, Fishbein M C, Cercek B M Forrester J S, Kim C-J, Berglund H. Siegel R J. Myocardial ischemia/infarction/thrombolysis: transcutaneous US augments lysis of arterial thrombi in vivo. *Circulation.* 1996; 94:775–778.
10. Kashyap A, Blinc A, Marder V J, Penney D P, Francis C W. Acceleration of fibrinolysis by US in a rabbit ear model of small vessel injury. *Thromb Res.* 1994; 76:475–485.
11. Birnbaum Y, Luo H, Nagai T, Fishbein M C, Peterson T M, Li S, Kricsfeld D, Porter T R, Siegel R J. Noninvasive in vivo clot dissolution without a thrombolytic drug: recanalization of thrombosed iliofemoral arteries by transcutaneous US combined with intravenous infusion of microbubbles. *Circulation.* 1998; 97:130–134.
12. Shlansky-Goldberg R D, Cines D B, Sehgal C M. Catheter-delivered US potentiates in vitro thrombolysis. *J Vasc Interv Radiol.* 1996; 7:313–320.
13. Sehgal C M, Leven R F, Shlansky-Goldberg R D. US-assisted thrombolysis. *Invest Radiol.* 1993; 28:939–943.
14. Haberl R L, Heizer M L, Marmarou A, Ellis E F. Laser-Doppler assessment of brain microcirculation: effect of systemic alterations. *Am J Physiol.* 1989; 256: 1247–1254.
15. Summaria L, Arzadon L, Bernabe P, Robbins K C. The interaction of streptokinase with human cat, dog, and rabbit plasminogens. *J Biol Chem.* 1974; 249:4760–4769.
16. Blinc A, Francis C W. Transport processes in fibrinolysis and fibrinolytic therapy. *Thromb Haemost.* 1996; 76:481–491.
17. Francis C W, Blinc A, Lee S, Cox C. US accelerates transport of recombinant tissue plasminogen activator into clots. *US Med Biol.* 1995; 21:419–424.
18. Siddiqi F, Blinc A, Braaten J, Francis C W. US increases flow through fibrin gels. *Thromb Haemost.* 1995; 73:495–498.
19. Braaten J V, Goss R A, Francis C W. US reversibly disaggregates fibrin fibers. *Thromb Haemost* 1997; 78:1063–1068.
20. Siddiqi F, Odrljin T M, Fay P J, Cox C, Francis C W. Binding of tissue-plasminogen activator to fibrin: Effect of US. *Blood* 1998; 91:2019–2025.
21. Nishioka T, Luo H. Fishbein M C, Cercek B, Forrester J S, Kim C-J, Bergima J, Siegel R L. Dissolution of thrombotic arterial occlusion by high intensity, low frequency US and dodecafluoropentane emulsion: An in vitro and in vivo study. *J Am Coll Cardiol.* 1997; 30:561–568.
22. Rosenschein U, Bernstein J J, DdiSegni E, Kaplinsky E, Bernheim J, Rozenzsajn L A. Experimental ultrasonic angioplasty: Disruption of atherosclerotic plaque and thrombi in vitro and arterial recanalization in vivo. *J Am Coll Cardiol.* 1990; 15:711–717.

23. Ariani M, Fishbein M C, Chae J S, Sadeghu H, Don-Michael A, Dubin S B, Siegel RJ. Dissolution of peripheral arterial thrombi by US. *Circulation.* 1991; 84:1680–1688.
24. Trubstein G, Engel C, Etzerl F, Sobbe H, Cremer H, Stumpff U. Thrombolysis by US. *Clin Sci Mol Med.* 1976; 51:697s–698s.
25. Eccleston D S, Cumpston G N, Hodge A J, Pearne-Rowe D, DonMichael T A. Ultrasonic coronary angioplasty during coronary artery bypass grafting. *J Am Coll Cardiol.* 1996; 78:1172–1175.
26. Rosenschein U, Rozenszajn L A, Kraus L, Marboe C C, Watkins J F, Rose E A, David D, Cannon P J, Weinstein J S. Ultrasonic angioplasty in totally occluded peripheral arteries: initial clinical, histological, and angiographic results. *Circulation.* 1991; 83:1976–1986.
27. Siegel RJ, Gaines P, Crew J R, Cumberland D C. Clinical trial of percutaneous peripheral US angioplasty. *J Am Coll Cardiol.* 1993; 22:480–488.
28. Rosenschein U, Gaul G, Erbel R, Amann F, Velasguez D, Stoerger H, Simon R, Gomez G, Troster J, Bartorelli A, Peiper M, Kyriakides Z, Laniado S, Miller H I, Cribier A, Fajedet J. Percutaneous transluminal therapy of occluded saphenous vein grafts. Can the challenge be met with US thrombolysis? *Circulation* 1999; 99:26–29.
29. Behrens S, Daffertshofer M, Spiegel D, Hennerici M. Low-frequency, low-intensity US accelerates thrombolysis through the skull. *US Med Biol.* 1999; 25:269–273.
30. Akiyama M, Ishibashi T, Yamada T, Furuhata H. Low-frequency US penetrates the cranium and enhances thrombolysis in vitro. *Neurosurgery* 1998; 43:828–833.
31. Stern M D, Lappe D L, Bowen P D, himosky J E, Holloway G A Jr, Keiser H R, Bowman R L. Continuous measurement of tissue blood flow by laser-Doppler spectroscopy. *Am J Physiol.* 1977; 232:441–448.
32. Corson M A, James N L, Latta S E, Nerem R M, Berk B C, Harrison D G. Phosphorylation of endothelial nitric oxide synthase in response to fluid shear stress. *Circ Res.* 1996; 9:984–991.
33. Uematsu M, Ohara Y, Navas J P, Nishida K, Murphy T J, Alexander R W, Nerem R M, Harrison D G. Regulation of endothelial cell nitric oxide synthase mRNA expression by shear stress. *Am J Physiol.* 1995; 269:1371–1378.
34. Christopherson K S. and Bredt D S. Nitric Oxide in Excitable Tissues: Physiological Roles and Disease. *J. Clin. Investig.* 1997; 100:2424–2429.
35. Bredt D S and Snyder S H. Nitric Oxide: A Physiologic Messenger Molecule. *Annu. Rev. Biochem.* 1994; 63:175–195.
36. Cooke J. P. and Dzau, V J. Derangements of the Nitric Oxide Synthase Pathway, L-arginine and Cardiovascular Diseases. *Circulation* 1997; 96:379–382.
37. Nakane M, Schmidt H H, Pollock J S, Forstermann U and Murad F. Cloned human brain nitric oxide synthase is highly expressed in skeletal muscle. *FEBS Lett.* 1993; 316:175–180.
38. Kobzik L, Reid M B, Bredt D S and Stamler J S. Nitric oxide in skeletal muscle. *Nature* 1994; 372:546–548.
39. Samdani. A F, Dawson T M, and Dawson V L. Nitric Oxide Synthase in Models of Focal Ischemia: *Stroke* 1997; 28:1283–1288.
40. Huang P L, Dawson T M, Bredt D S, Snyder S H, Fishman M C. Targeted Disruption of the Neuronal Nitric Oxide Synthase Gene. *Cell* 1993; 75:1273–1286.
41. Chung E D, Curtis G, Chen P A, Marsden R, Twells R, Xu W, and Gardiner M. Genetic Evidence for the Neuronal Nitric Oxide Synthase Gene (NOS1) as a Susceptibility Locus for Infantile Pyloric Stenosis. *Am. J. Hum. Genet.* 1996; 58:363–370.
42. Iadecola C, Zhang F, and Xu X. Role of nitric oxide synthase-containing vascular nerves in cerebrovasodilation elicited from cerebellum. *Am. J. Physiol.* 1993; 264:R738–R746.
43. Bredt D S, Hwang P M, and Snyder, S H. Localization of nitric oxide synthase indicating a neural role for nitric oxide. Nature 1990; 347:768–770.
44. Welch K M. Drug therapy of migraine [see comments]. *N. Engl. J. Med.* 1993; 329: 1476–1483.
45. Burnett A L, Tillman S L, Chang T S, Epstein J I, Lowenstein C J, Bredt D S, Snyder S H, Walsh P C. Immunohistochemical localization of nitric oxide synthase in the autonomic innervation of the human penis. *J. Urol.* 1993; 150:73–76.
46. Raijfer J, Aronson W J, Bush P A, Dorey F J, and Ignarro L J. Nitric oxide as a mediator of relaxation of the corpus cavernosum in response to nonadrenergic, noncholinergic neurotransmission. *N. Engl. J. Med.* 1992; 326:90–94.
47. Burnett A L, Nelson R J, Calvin D C, Liu J X, Demas G E, Klein S L, Kriegsfeld L J, Dawson V L, and Snyder S H. Nitric oxide-dependent penile erection in mice lacking neuronal nitric oxide synthase. *Mol. Med.* 1996; 2:228–296.
48. Vernet D, Cai L, Garban H, Babbitt M L, Murray F T, Raijfer J, and Gonzalez-Cadavid N F. Reduction of penile nitric oxide synthase in diabetic BB/WORdp (type I) and BBZ/WORdp (type II) rats with erectile dysfunction. *Endocrinology* 1995; 136:5709–5717.
49. Carrier S, Nagaraju P, Morgan D M, Baba K, Nunes L, and Lue T F. Age decreases nitric oxide synthase-containing nerve fibers in the rat penis. *J. Urol.* 1997; 157:1088–1092.
50. Penson D F, Ng C, Cai L, Raijfer J, and Gonzalez-Cadavid N F. Androgen and pituitary control of penile nitric oxide synthase and erectile function in the rat. *Biol. Reprod.* 1996; 55:567–574.
51. Schuman E M, and Madison D V. Nitric oxide and synaptic function. *Annu. Rev. Neurosci.* 1994; 17:153–183.
52. Shibuki K, and Okada D. Endogenous nitric oxide release required for long-term synaptic depression in the cerebellum. *Nature* 1991; 349:326–328.
53. Son H, Hawkins R D, Martin K, Kiebler M, Huang P L, Fishman M C, and Kandel E R. Long-term potentiation is reduced in mice that are doubly mutant in endothelial and neuronal nitric oxide synthase. *Cell.* 1996; 87:1015–1023.
54. Silvagno F, Xia H, and Bredt D S. Neuronal nitric oxide synthase-micro, an alternatively spliced isoform expressed in differentiated skeletal muscle. *J. Biol. Chem.* 1996; 271:11204–11208.
55. Lee K H, Back M Y, Moon K Y, Song W K, Chung C H, Ha D B, and Kang M S. Nitric oxide as a messenger molecule for myoblast fusion. *J. Biol. Chem.* 1994; 269: 14371–14374.
56. Wang T, Xie Z, and Lu B. Nitric oxide mediates activity-dependent synaptic suppression at developing neuromuscular synapses. *Nature* 1995; 374:262–266.
57. Roberts C K, Barnard R J, Scheck S H, and Balon T W. Exercise-stimulated glucose transport in skeletal muscle is nitric oxide dependent. *Am. J. Physiol.* 1997; 273: E220–E225.

What is claimed:
1. A method of treating a patient with a neurodegenerative disease, said method comprising:

selecting a patient having a neurodegenerative disease selected from the group consisting of Parkinson's disease, amyotrophic lateral sclerosis, and Huntington's disease and applying ultrasound to tissue diseased by the neurodegenerative disease under conditions effective to increase nitric oxide production in the tissue.

2. A method according to claim 1, wherein said ultrasound is applied to surgically exposed tissue.

3. A method according to claim 1, wherein said ultrasound is applied through skin overlying the tissue.

4. A method according to claim 1, wherein said ultrasound is applied to the tissue with a catheter.

5. A method according to claim 1, wherein said applying comprises:

providing an ultrasound transducer;

placing said ultrasound transducer adjacent to said tissue; and subjecting said tissue to ultrasound treatment with said ultrasound transducer.

6. A method according to claim 5, wherein said ultrasound transducer operates at a frequency of from about 10 to 300 kHz.

7. A method according to claim 5, wherein said ultrasound transducer operates at an intensity of from about 0.25 to 2 W/cm$^2$.

* * * * *

UNITED STATES PATENT AND TRADEMARK OFFICE
CERTIFICATE OF CORRECTION

Page 1 of 1

PATENT NO. : 7,211,054 B1
APPLICATION NO. : 09/435286
DATED : May 1, 2007
INVENTOR(S) : Francis et al.

It is certified that error appears in the above-identified patent and that said Letters Patent is hereby corrected as shown below:

IN THE SPECIFICATION

At col. 1, lines 8-11, delete:

"The subject matter of this application was made with support from the United States Government under Grants No. HL-30616 from the National Institutes of Health. The United States Government may retain certain rights."

and insert:

-- This invention was made with government support under HL050497 awarded by National Institutes of Health. The government has certain rights in the invention. --

Signed and Sealed this
Tenth Day of March, 2015

Michelle K. Lee
*Deputy Director of the United States Patent and Trademark Office*